United States Patent [19]

Crovetti et al.

[11] Patent Number: 5,051,450
[45] Date of Patent: Sep. 24, 1991

[54] DIIODOMETHYLSULFONE INSECTICIDES

[75] Inventors: Aldo J. Crovetti, Lake Forest; Brian E. Melin, Glencoe; Robert A. Smith, Lindenhurst; Francois M. Hubert Casati, Highland Park, all of Ill.

[73] Assignee: Angus Chemical Company, Northbrook, Ill.

[21] Appl. No.: 441,126

[22] Filed: Nov. 22, 1989

Related U.S. Application Data

[63] Continuation of Ser. No. 087,495, Aug. 19, 1987, abandoned, and a continuation-in-part of Ser. No. 904,330, Sep. 5, 1986, abandoned.

[51] Int. Cl.$^5$ .................... A01N 33/02; A01N 37/10; A01N 37/18; A01N 41/10
[52] U.S. Cl. .................................. 514/709; 514/570; 514/629; 514/646; 514/711
[58] Field of Search ............... 514/709, 711, 570, 629, 514/646

[56] References Cited

U.S. PATENT DOCUMENTS

| | | | |
|---|---|---|---|
| 3,615,745 | 10/1971 | Crovetti et al. | 106/15 |
| 3,657,353 | 4/1972 | Crovetti et al. | 260/607 A |
| 3,663,623 | 5/1972 | Crovetti et al. | 260/607 A |
| 3,927,100 | 12/1975 | Crovetti et al. | 260/578 |
| 4,185,120 | 1/1980 | Smith | 260/607 A |

FOREIGN PATENT DOCUMENTS

| | | | |
|---|---|---|---|
| 1473116 | 3/1967 | France | 514/709 |
| 1584546 | 12/1969 | France | 514/709 |
| 60-239402 | 11/1985 | Japan | 514/709 |

OTHER PUBLICATIONS

Hedley et al. Int. Biodeterior Bull. vol. 15 (1), pp. 9–18 (1979).
Nakamura et al. Journal of the Society of Material, Science, Japan pp. 929–934 (1983).

*Primary Examiner*—Allen J. Robinson
*Attorney, Agent, or Firm*—Leydig, Voit & Mayer

[57] ABSTRACT

A composition comprising a compound of the formula:

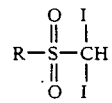

wherein R is $R_1(CH_2)_n$, wherein n is 0 to 4 and $R_1$ is loweralkyl, phenyl, monoloweralkylphenyl, monohalophenyl, nitrophenyl, aminophenyl, acetamidosubstituted phenyl, $(CH_2)_m COOH$-substituted phenyl wherein m is 1 to 3, disubstitutedhalophenyl, (halo)(nitro)phenyl, (nitro)(loweralkyl)phenyl, (halo)(loweralkyl)phenyl or disubstitutedloweralkylphenyl, is effectively used for the control of termites, cockroaches and ants.

10 Claims, No Drawings

DIIODOMETHYLSULFONE INSECTICIDES

This application is a continuation, of application Ser. No. 087,495, filed Aug. 19, 1987, now abandoned, which application is a continuation-in-part of U.S. patent application Ser. No. 904,330, filed Sept. 5, 1986, now abandoned.

BACKGROUND OF THE INVENTION

This invention relates to insecticidal compositions comprising diiodomethylsulfone derivatives and to the use of such derivatives for the control of termites, cockroaches, and ants.

Subterranean termites are of considerable economic importance throughout the United States, and costs for damage and control may exceed an estimated $750 million annually. Much of this cost is attributable to the Reticulitermes genus, which encompasses the most widespread termites and which includes the species *Reticulitermes virginicus* and *Reticulitermes flavipes*. Several other subterranean termite species are also extremely destructive, but their impact is limited by their distribution. For example, *Heterotermes aureus* is a major pest in the desert Southwest.

The Formosan subterranean termite, *Coptotermes formosanus*, is distributed throughout many of the tropical, subtropical and temperate regions of the world, including China, Taiwan, Japan, Hawaii, Guam, Midway Island, South Africa, Sri Lanka, and parts of the continental United States. Within the past three decades, it has been reported in Louisiana, Texas, South Carolina, Florida, Alabama, Mississippi, and Tennessee. In 1984 costs for control of this insect were $120 million in China, $400 million in Japan, %60 million in Hawaii and $5-6 million in the aforementioned Southeastern states. The Formosan termite is extremely difficult to control, once established, and is often considered the most destructive structural pest. It will feed on any cellulosic material. It not only causes serious damage to structures and other wooden materials such as utility poles, but also is known to attack living vegetation. This pest also attacks and penetrates non-cellulosic items such as electric and telephone cables, plaster, and plastics confronted in its foraging path.

Carpenter ants in natural environments are decomposers, commonly found in trees and logs. Several species, however, have extended their habitat to wooden structures used by man. In 1985 it was reported that 78% of the structural infestations investigated in the state of Washington were caused by *Camponotus modoc*. In the Northeast, two species attack wooden structures: the black carpenter ant, *Camponotus pennsylvanicus*, and the New York or red carpenter ant, *Camponotus novaeboracensis*. Carpenter ants are costly pests. In 1982 it was estimated that residents of New Jersey are spending at least $25 million per year on carpenter ant control around the home. Carpenter ants are also a major source of damage to wooden utility poles.

The cockroach is probably the most obnoxious insect known to man. There is a considerable body of evidence to incriminate a number of species of cockroaches as potential carriers of disease. Cockroaches are regarded as loathsome intruders for many reasons: their speed and unpredictable direction of movement, the enormous numbers to which populations can increase if left undisturbed, and their habit of tainting with a characteristic odor, and fouling with excrement, all food and surfaces with which they come into contact. Finally, because cockroaches are usually associated with poor standards of hygiene, their presence is psychologically disturbing and may cause considerable mental distress. The most prevalent cockroach in the United States is the European cockroach, *Blatella germanica*.

The insecticidal compositions of the present invention have been shown to be effective in controlling the Formosan termite, domestic or Reticulitermes termites, carpenter ants, other varieties of ants including imported fire ants (*Solenopsis saevissima*), and cockroaches. Other insects for which these compositions are believed to be efficacious include the pharaoh ant (*Monomorium pharaonis*); the powder post beetle (*Lyctus brunneus*) and the wood-destroying beetles (*Hylotrupes bajulus* and *Anobium punctatum*); and the fungus-growing termites (Macrotermitinae), which are agricultural pests in Africa and India.

DISCLOSURE OF THE INVENTION

A composition comprising a compound of the formula:

$$R-\underset{\underset{O}{\|}}{\overset{\overset{O}{\|}}{S}}-\underset{\underset{I}{|}}{\overset{\overset{I}{|}}{C}}H$$

wherein R is $R_1(CH_2)_n$, wherein n is 0 to 4 and $R_1$ is loweralkyl, phenyl, monoloweralkylphenyl, monohalophenyl, nitrophenyl, aminophenyl, acetamido-substituted phenyl, $(CH_2)_m COOH$-substituted phenyl wherein m is 1 to 3, disubstitutedhalophenyl, (halo)(nitro)phenyl, (nitro)(loweralkyl)phenyl, (halo)(loweralkyl)phenyl or disubstituted-loweralkylphenyl, is effectively used for the control of termites, cockroaches and ants.

As used herein, the term "ppm" means parts by weight of active ingredient per million parts by weight of finished product (liquid or solid form).

As used herein, the term "loweralkyl" means straight and branched chain $C_1$ to $C_5$ alkyl groups.

As used herein, the term "halo" refers to Cl, Br, F or I.

As used herein, the term "disubstitutedhalophenyl" refers to

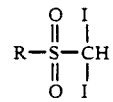

wherein X is halo.

As used herein, the term "(halo)(nitro)phenyl" refers to

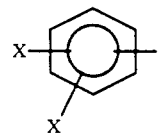

wherein X is halo.

As used herein, the term "(nitro)(loweralkyl)phenyl" refers to

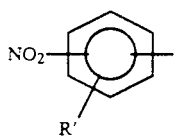

wherein R' is loweralkyl.

As used herein, the term "(halo)(loweralkyl)phenyl" refers to

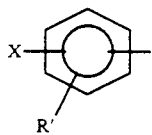

wherein X is halo and R' is loweralkyl.

As used herein, the term "disubstitutedloweralkylphenyl" refers to

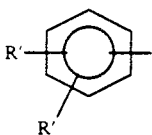

wherein R' is loweralkyl.

The most preferable compound is p-tolyl-diiodomethylsulfone.

The compounds of the present invention can be used in the form of compositions which are prepared by admixing a compound of the invention with one or more inert diluents or carriers, such as adjuvants or modifiers, to provide compositions in the form of dusts, wettable powders, high-strength concentrates, aqueous or nonaqueous dispersions, or baits. Baits are prepared by combining the compound with a liquid or solid food source attractive to the insect sought to be controlled. Thus, the compounds of this invention can be used with a carrier or diluent agent such as a finely-divided solid, an organic liquid, water, a wetting agent, a dispersing agent, an emulsifying agent, or any suitable combination of these. Similarly, these compounds may be combined with other insecticides in an advantageous manner.

The compositions, especially liquids and wettable powders, may contain surfactants in amounts sufficient to render a given composition readily dispersible in water or in oil. The surfactant used in this invention can be a wetting, dispersing or an emulsifying agent which will assist dispersion of the compound. The surfactant can include anionic, cationic and nonionic agents.

Suitable surfactants for use in compositions of the present invention include polyethylene glycol fatty acid esters and fatty alkylol amide condensates, alkylarylsulfonates, fatty alcohol sulfates, dialkyl esters of sodium sulfosuccinate, fatty acid esters of sodium isothionate, polyoxyethylene ethers and thioethers, and long-chain quaternary ammonium chloride compounds. Surface-active dispersing agents such as salts of lignin sulfonic acids, low-viscosity methyl cellulose, and polymerized sodium salts of alkylnaphthalenesulfonic acids are also suitable.

Among the more preferred surfactants are the anionic and nonionic types. Among the anionic surfactants, preferred ones are alkali metal or amine salts of alkylbenzenesulfonic acids such as dodecylbenzenesulfonic acid; sodium lauryl sulfate, alkylnaphthalenesulfonates, sodium N-methyl-N-oleoyltaurate, oleic acid ester of sodium isothionate, dioctyl sodium sulfosuccinate, and sodium dodecyldiphenyloxide disulfonate. Among the nonionic compounds, preferred members are alkylphenoxypoly (ethyleneoxy) ethanols such as nonylphenol adducts with ethylene oxide; polyethylene oxide adducts to long-chain aliphatic alcohols such as trimethylnonyl polyethylene glycol ethers, polyethylene oxide adducts of fatty and rosin acids, long-chain alkyl mercaptan adducts with ethylene oxide, and polyethylene oxide adducts with sorbitan fatty acid esters.

In general, less than 10 percent by weight of the surfactants will be used in compositions of this invention, and ordinarily the amount of surfactants will range from one to 5 percent but may even be less than one percent by weight.

The compositions of this invention may be in the form of wettable powders, suspension concentrates, dusts, granules, emulsifiable concentrates, aerosols, or baits as discussed hereinbelow. The precise form and concentration of a compound in accordance with the invention, of course, will depend upon the intended use of the composition.

In general, compositions intended for use in killing termites will contain from about 25 ppm to about 4,000 ppm of the active ingredient, with a concentration of about 25 ppm to about 800 ppm preferred for Reticulitermes termites and a concentration of about 200 ppm to about 4,000 ppm preferred for Formosan termites. Compositions intended for use in killing cockroaches will ordinarily contain from about 10,000 ppm to about 80,000 ppm of the active ingredient, while those intended for use in killing ants will range from about 10,000 ppm to about 40,000 ppm.

(A) Wettable Powders

Wettable powders are water-dispersible compositions containing the active material, an inert solid extender, and one or more surfactants to provide rapid wetting and to prevent flocculation of the composition upon suspension in water.

The inert extenders which are preferred for use in the wettable powders of this invention may be of either mineral or non-mineral origin.

The classes of extenders suitable for the wettable powder formulations of this invention include the natural clays, diatomaceous earth, and synthetic mineral fillers derived from silica and silicate. Preferred fillers for this invention are kaolinites, attapulgite clay, montmorillonite clays, synthetic silicas, synthetic magnesium silicate, and calcium sulfate dihydrate. The most preferred non-mineral filler is lactose.

Among the preferred surfactants are the nonionic and anionic types. Those most suitable for the preparation of the dry, wettable products of this invention are solid forms of compounds known to the art as wetters and dispersants. Occasionally a liquid, nonionic surfactant may serve as both a wetter and dispersant.

The most preferred wetting and dispersing agents are alkylbenzene- and alkylnaphthalenesulfonates; sulfated fatty alcohols; long-chain acid esters of sodium isothionate; esters of sodium sulfosuccinate; sulfated or sulfonated fatty acid esters; petroleum sulfonates; sulfonated vegetable oils; and ditertiary acetylenic glycols. Preferred dispersants are methylcellulose, polyvinyl alcohol, lignin sulfonates, polymeric alkylnaphthalenesulfonates, polymethylene bisnaphthalenesulfonate, sodium N-methyl-N-(long chain acid)taurates and polyethylene oxide adduct with sorbitan fatty acid esters.

Wetting and dispersing agents in these preferred wettable powder compositions of this invention are usually present at concentrations of about 0.5 weight-percent to 5 weight-percent. The inert extender then completes the formulation. Where needed, b 0.1 weight-percent to 5 weight-percent of the extender may be replaced by an anti-foaming and free flow agent.

Thus, wettable powder formulations of the invention will usually contain from about 25 to 90 weight-percent active material, from 0.5 to 2.0 weight-percent wetting agent, from 0.25 to 5.0 weight-percent dispersant, and from 9.25 to 74.25 weight-percent inert extender, as these terms are described above.

When the wettable powder contains a free-flow agent or an anti-foaming agent or both, the free-flow agent will not exceed about 4 to 5 percent by weight of the composition, and the anti-foaming agent will not exceed about 0.5 percent by weight of the composition, both replacing equivalent amounts of the inert extender.

These compositions may contain, in addition to a surfactant, finely divided inert diluents such as talcs, natural clays including attapulgite clay and kaolinite clay, pyrophyllite, diatomaceous earth, synthetic fine silicas, calcium silicate, carbonates, and lactose.

Preferred diluents are clays of hydrated aluminum silicate, hydrated aluminum magnesium silicate and hydrated aluminum magnesium iron silicate.

The amount of the finely divided inert solid diluent can vary widely but will generally range from about 10 to 98 percent by weight of the composition.

Wettable compositions are prepared by blending the ingredients and grinding in a hammer mill or an air attrition mill or similar device. The particle size can vary considerably but will ordinarily be screened so that the finished formulation has a particle size of 50 microns or less.

(B) High-Strength Compositions and Aqueous Suspension Concentrates

High-strength compositions generally consist of 90 to 99.5 weight-percent active ingredient and 0.5 to 10 weight-percent of a liquid or solid surfactant. Up to approximately half of the surfactant may be replaced by an anti-caking agent such as a synthetic silica. Such high-strength compositions can often be used in a manner similar to the wettable powders but they are also suitable for further formulation.

The aqueous suspension concentrates are prepared by mixing together and milling an aqueous slurry of water-insoluble active ingredient in the presence of surfactants, dispersing agents, anti-foam agents, viscosity stabilizers, etc. Thus, there is obtained a concentrated slurry, or aqueous suspension, of very finely divided particles, all below 10 microns in size. The advantage of the extremely small particle size of the active ingredient is that, upon dilution and spraying, a very uniform coverage is obtained.

These aqueous suspension concentrates will contain from 15 to 55 weight-percent of active ingredient and from 40 to 70 weight-percent water, with the remainder comprising surfactants, dispersing agents, suspending agents and anti-foam agents.

Suspensions in organic liquids can be prepared in a similar manner, e.g., by replacing the water with mineral oil.

(C) Dusts

Dusts are dense powder compositions intended for application in dry form and characterized by their free-flowing and rapid settling properties whereby they are not readily windborne to areas where their presence is not desired. They contain primarily an active material and a dense, free-flowing, solid extender.

Their performance is sometimes aided by the inclusion of a wetting agent, and convenience in manufacture frequently demands the inclusion of an inert, absorptive grinding aid. For the dust compositions of this invention, the inert extender may be of either plant or mineral origin, the wetting agent is preferably anionic or nonionic, and suitable absorptive grinding aids are of mineral origin.

Suitable classes of inert solid extenders for use in the dust compositions are those organic or inorganic powders which possess high bulk density and are very free-flowing. They are also characterized by possessing relatively low surface areas and are poor in liquid absorption. Suitable classes of grinding aids are natural clays, diatomaceous earth, and synthetic mineral fillers derived from silica or silicate.

Preferred inert solid extenders for the dusts of this invention are micaceous talc, pyrophyllite, kaolinate and dense kaolin clays, tobacco dust and ground calcium phosphate rock such as that known as "Phosphodust."

Preferred grinding aids are attapulgite clay, diatomaceous earth, silica, synthetic fine silica and synthetic calcium and magnesium silicates.

Preferred wetting agents are those previously described under wettable powder formulations.

The inert solid extenders in the dusts of this invention are usually present in concentrations of from about 30 to 90 weight-percent of the total composition. The grinding aid will usually constitute from about 5 to 50 weight-percent of the composition, and the wetting agent will constitute from about 0 to 1.0 weight-percent of the composition. Dust compositions may also contain other surfactants such as dispersing agents in concentrations of up to about 0.5 weight-percent.

The wettable powders described above can also be used in the preparation of dusts. While such wettable powders could be used directly in dust form, it is more advantageous to dilute them by blending with the dense dust diluent. In this manner, dispersing agents and anti-foam agents may also be found as components of a dust.

Thus, the dust compositions of this invention will usually comprise about 5 to 20 weight-percent active material, 5 to 50 weight-percent absorptive filler, 0 to 1.0 weight-percent wetting agent, and about 30 to 90 weight-percent dense, free-flowing dust diluent, as these terms are used herein. Such dust formulations may contain, in addition, minor amounts of dispersants and anti-foam agents, derived from the wettable powders used to make the dusts.

(D) Granules

Compositions can also be formulated into granules. Such compositions will usually comprise diluent from 65 to 99 weight-percent and active ingredient from 1 to 35 weight-percent. For preparation of granules the compound can be dissolved in a solvent, and this solution can be sprayed over pre-formed clay granules, expanded vermiculite or the like, while agitating the mixture to distribute the active ingredient over and throughout the granular mass. Such granules can range in particle size of from +60 mesh to +4 mesh, and an active ingredient content of 1 to 6 weight-percent is preferred. Granules of even smaller size may be prepared similarly and applied from appropriately designed equipment. It is also possible to make such granules by mixing the finely divided diluent and finely divided compounds, for instance by grinding together, and then forming granules by adding water, tumbling and drying the resulting spheres. It is also possible to mix a finely divided compound with granular carriers such as attapulgite or vermiculite and then bind the active ingredient to ingredient carrier by spraying the whole with a non-volatile liquid.

(E) Suspension Concentrates

Suspension concentrates can be prepared by wet-milling the ingredients, e.g., by ball milling or by sand-grinding, such that fine particles of the active compounds within the scope of this invention will be dispersed evenly in a diluent. Such compositions normally contain from 15 to 50 weight-percent active ingredient and are characterized by having particles substantially less than 10 microns in diameter.

(F) Emulsifiable Suspensions

Water-emulsifiable oil compositions may also be employed with one or more of the compounds of this invention. In these compositions, surfactants and an oil form a liquid which can be conveniently poured and measured. Such liquid concentrates can be mixed with water at the point of application. Such compositions have the advantage that the oil will often act as a foam inhibitor and thus reduce the tendency for large amounts of surfactants to form objectionable foam. These oil formulations constitute dispersions of the compounds in finely divided form in nonsolvent carriers. A nonsolvent carrier is an oil in which the compounds have low solubility, for instance, less than about 0.1% at 25° C. Many aliphatic hydrocarbons, vegetable and mineral oils are examples of such nonsolvent carriers.

In these emulsifiable oil suspensions, the compounds will be present in amounts ranging from 5 to 35 percent by weight. Upon mixing with water at the point of application, the oil suspension will be diluted; thus, in the final formulation the active agent will be present in amounts ranging from 0.5 to 2 percent by weight.

(G) Aerosols

Still another liquid formulation which is particularly convenient for small scale use is the "aerosol" formulation, which is packaged under pressure in a suitable container. The liquid phase may be a suspension, emulsion, or solution. For simplicity in preparation and use, solutions are preferred. The pressure may be supplied by low-boiling liquid such as propane or chlorofluorocarbons, or by relatively insoluble gases such as carbon dioxide or nitrous oxide. The chlorofluorocarbons are preferred for a combination of good solvent power and lack of flammability.

It is preferred that the active ingredient remain totally dissolved in all solution formulations at 0° C. or as low a storage temperature as can be resonably expected for prolonged periods. In order to insure this, co-solvents, which may be water-miscible even in emulsifiable concentrates, may also be included in the formulations.

Organic liquids suitable for preparation of solutions, suspensions and emulsifiable concentrates of the compounds of this invention include alcohols, glycols, mono- and dialkyl ethers of ethylene glycol and its derivatives, carbitols, ketones, esters, sulfoxides, sulfones, sulfamides, amides, paraffinic hydrocarbons, aromatic hydrocarbons and halogenated hydrocarbons.

(H) Baits

Baits can be prepared by blending the active ingredient with a product known to attract the insect, e.g., some form of food source (liquid or solid). For instance, in the case of termites, pieces of wood may be impregnated with a solution of the compound. In some instances, partially decayed wood may be preferred, or even paper or cardboard.

The following examples will illustrate the preparation and testing of the compositions of the invention:

EXAMPLE 1

Preparation of p-Tolyl-diiodomethylsulfone

This compound may be made as disclosed in U.S. Pat. No. 3,615,745, issued Oct. 26, 1971; U.S. Pat. No. 3,657,353, issued Apr. 18, 1972; or U.S. Pat. No. 3,663,623, issued May 16, 1972; all of which are incorporated herein by reference.

Generally, the compounds of the present invention may be prepared by halogenating R-sulfonyl acetic acids with a sodium hypohalite in an alkaline aqueous solution followed by decarboxylation. The reaction may be represented as follows:

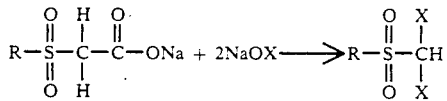

wherein X represents a halogen and R is as stated hereinabove.

EXAMPLE 2

Imported Fire Ant Bait Toxicant Tests (Solenopsis invicta Buren)

Tests were conducted in 30 ml disposable plastic medicine cups (40 mm ID at the top, tapering to 32 mm ID at the bottom, 38 mm high). A hole (6 mm diameter) was drilled through the bottom of each cup, and a layer of dental labstone (Ranson and Randolph Co., Toledo, Ohio) was poured over the bottom. The labstone covered the hole and served as a wick to draw up water when the cup was placed on a saturated ¼" foam pad. The cups were placed in a tray and covered with a sheet of clear glass to prevent rapid evaporation of the water from the foam pad. Moisture was necessary to keep the humidity in the cups high and thereby prevent desiccation of the ants.

Twenty worker ants from laboratory colonies deprived of food for 14 days were placed in each test chamber approximately 24 hours preceding the start of the test. This pretreatment holding period allowed time for recovery of the ants from handling and for orientation to the containers. Only those worker ants collected from the inside of rearing cells containing brood were used in the tests.

A quantity of p-tolyl-diiodomethylsulfone (prepared in Example 1) was dissolved directly in the food material, once-refined soybean oil. This toxic solution was offered to the ants on cotton swabs saturated with the material and placed in the test chamber in small vial caps.

The ants were allowed to feed as desired on the toxic bait for 24 hours. After this exposure period, the toxicant was removed from the chamber and the ants remained without food for an additional 24 hours. At the end of this time, new vial caps containing cotton swabs saturated with soybean oil were placed in the chamber and left for the remainder of the test period. Knockdown and mortality counts were made at intervals of 1, 2, 3, 6, 8, 10 and 14 days following initial exposure. Each test consisted of three replications. Room temperature was maintained at 80°±2° F.

Data obtained are reported in Table 1 below.

TABLE 1

Effectiveness of p-tolyl-diiodomethylsulfone as a bait toxicant against red imported fire ants

| Chemical | Conc. (ppm) | Percent mortality (cumulative) after indicated number of days | | | | | | |
|---|---|---|---|---|---|---|---|---|
| | | 1 | 2 | 3 | 6 | 8 | 10 | 14 |
| | | Test 1 | | | | | | |
| Example 1 | 100 | 5 | 5 | 8 | 8 | 8 | 8 | 12 |
| | 1,000 | 5 | 5 | 5 | 7 | 22 | 27 | 33 |
| | 10,000 | 10 | 15 | 22 | 27 | 32 | 37 | 38 |
| Mirex* (control) | 100 | 0 | 0 | 3 | 3 | 7 | 25 | 30 |
| | 1,000 | 3 | 5 | 10 | 58 | 83 | 88 | 93 |
| | 10,000 | 8 | 53 | 83 | 100 | | | |

*Dodecachlorooctahydro-1,3,4-metheno-1H-cyclobuta(cd) pentalene

EXAMPLE 3

Carpenter Ant Choice Tests

Camponotus pennsylvanicus and novaeboracensis

Laboratory colonies of carpenter ants were housed in plastic 9"×12" shoe boxes. The sides of the boxes were coated with a liquid Teflon ® nonstick coating to prevent the ants from escaping. Each box contained a large test tube with a wet cotton plug in the bottom, which served as a nest. The boxes were covered and placed in an incubator at 22° C. with a 12:12 hour light-dark cycle.

A 50:50 mix of wildflower honey and distilled water (hereinafter referred to as "honey-water") was prepared. A micronized aqueous suspension of p-tolyl-diiodomethylsulfone (Example 1) was prepared, in accordance with the procedures described in section (B), supra. Because both the honey-water and the aqueous suspension were sticky materials difficult to measure accurately with a pipette, the following procedure was used in this experiment: An empty, sterile polystyrene petri dish (dimensions 100 mm×15 mm) was tared on a Mettler balance. The p-tolyl-diiodomethylsulfone was placed in the dish and weighed. The honey-water was added and the total weight taken. The weight of the p-tolyl-diiodomethylsulfone was then subtracted to obtain the weight of the honey-water. The mixture was stirred and soaked onto a 1"×1" square of cellulose sheeting.

The treated cellulose square was placed on one half of a petri dish, and a cellulose square that had been soaked in plain honey-water was placed on the other half. The number of workers feeding on each side was recorded every minute or every five minutes, depending upon the activity level of the ants, for 25 minutes.

The following treatments were used:

| Trial | p-Tolyl-diiodomethylsulfone Suspension (40% active) (grams) | Honey-water (grams) | Conc. Active Ingredient (ppm) |
|---|---|---|---|
| 1 | approx. 0.5 | approx. 1.5 | 100,000 |
| 2 | 0.218 | 2.99 | 27,400 |
| 3 | 0.023 | 2.04 | 4,500 |
| 4 | 0.092 | 2.36 | 14,700 |

In trial 1, 14 *Camponotus novaeboracensis* workers were used. They spent a total of 6 ant-minutes on the treated side and 11 ant-minutes on the untreated side. Observations suggested that the ants were detecting something in the treatment because they would approach the cellulose in the usual manner but would feed only briefly.

Trials 2 and 3 were both performed with 15 novaeboracensis workers. In neither trial did the ants indicate any hesitation in feeding on the treated side. The ants in trial 2 spent 7 ant-minutes on the treated side and 10 ant-minutes on the untreated side. In trial 3 they spent 2 ant-minutes on the treated side and 3 ant-minutes on the untreated side.

Trial 4 was performed with 10 *Camponotus pennsylvanicus* workers. Again, the ants showed no behavioral preferences, and spent 9 ant-minutes on the treated side and 6 ant-minutes on the treated side.

It was concluded from this that treatments of about 15,000 ppm of p-tolyl-diiodomethylsulfone in honey-water is appropriate for laboratory trials.

EXAMPLE 4

Carpenter Ant Laboratory Trials

One queenright *Camponotus pennsylvanicus* colony (colony 1) and five queenright *Camponotus novaeboracesis* colonies (colonies 2 through 6) were pared down to about 200 workers. A petri dish containing treated cellulose sheeting was given to each of these colonies. One colony was given a dose much higher than 15,000 ppm p-tolyl-diiodomethylsulfone in honey-water for purposes of comparison. One week later the treatment was removed and the colonies were fed as usual on honey-water and fly pupae for the remainder of the experiment.

The following treatments were used:

| Colony | Active Ingredient (grams) | Honey-water (grams) | Total | Conc Active Ingredient (ppm) |
|---|---|---|---|---|
| 9D | 0.215 | 2.176 | 2.391 | 90,000 |
| 4D | 0.043 | 2.154 | 2.197 | 19,600 |
| 8DP | 0.097 | 5.804 | 5.901 | 16,400 |
| 8DT | 0.008 | 2.161 | 2.169 | 3,700 |
| 6D | 0.040 | 2.270 | 2.310 | 17,300 |
| 7D | 0.010 | 2.099 | 2.109 | 4,700 |

The results are given in Table 2 below.

TABLE 2

| Number of Days | Number of ants surviving in each treated colony | | | | | |
|---|---|---|---|---|---|---|
| | Concentration p-Tolyl-diiodomethylsulfone (ppm) | | | | | |
| | 90,000 | 19,600 | 16,400 | 3,700 | 17,300 | 4,700 |
| 0 | 210 | 214 | 133 | 232 | 219 | 205 |
| 6 | 208 | 158 | 69 | 230 | 147 | 195 |

TABLE 2-continued

| Number of Days | Number of ants surviving in each treated colony | | | | | |
|---|---|---|---|---|---|---|
| | Concentration p-Tolyl-diiodomethylsulfone (ppm) | | | | | |
| | 90,000 | 19,600 | 16,400 | 3,700 | 17,300 | 4,700 |
| 15 | 208 | 135 | 48 | 208 | 126 | 170 |
| 19 | 190 | 37 | 2 | 146 | 32 | 92 |
| 29 | 100 | 8 | 0 | 101 | 2 | 1 |
| 36 | 37 | 0 | 0 | 5 | 0 | 0 |
| 43 | 2 | 0 | 0 | 0 | 0 | 0 |
| 49 | 0 | 0 | 0 | 0 | 0 | 0 |

Basically, all the colonies were killed. A control colony kept in the same incubator did not show any mortality. It was evident that the smaller workers (minors) were killed first, and that the colonies with a larger proportion of major workers lived longer. The queens were always among the last individuals alive.

EXAMPLE 5

Testing Against Formosan Termites

One hundred *Coptotermes formosanus* termites (92 workers and 8 soldiers) collected from a field colony in Hallandale, Fla., were placed in petri dishes containing filter papers (Whitman No. 1, 5.5 cm) impregnated with the compound of Example 1 at concentrations of 0, 1,000, 2,000 and 4,000 ppm in acetone (which was then evaporated), and moistened with deionized water. Three replicates were prepared for each treatment, for a total of 12 experimental units. All units were held at $29° \pm 1°$ C. for 24 hours. After forced feeding on p-tolyl-diiodomethylsulfone (prepared in Example 1) for 24 hours, the termites were transferred to petri dishes containing untreated filter papers moistened with deionized water. Observations were made daily for 17 days. Dead and moribund individuals were counted and removed from the petri dishes. Percent mortality of workers was the response variable evaluated.

Results are presented in Table 3. Control mortality at 17 days was $15.0 + 4.2\%$. Mortality from the test compound was concentration-dependent and characterized by its delayed action on *Coptotermes formosanus*. This delayed action, or latent effect, is an extremely important factor in the overall efficacy of a termiticide. Termites, like ants and bees, are social insects living in complex, ordered communities. Because soldier insects must be fed and groomed by worker insects, it is more advantageous for a termiticide to be slow-acting than fast-acting. The reason for this is that a termite exposed to the poison will live long enough to bring it back to the termite colony, where it will be spread by termites feeding and grooming each other. In addition, a fast-acting poison will create an avoidance reaction, as live termites will seal off or avoid treated areas containing large numbers of dead termites.

TABLE 3

Percent mortality (cumulative) after indicated number of days (p-tolyl-diiodomethylsulfone vs. *C. formosanus*)

| Concentration | No. of Days | | | | | | | |
|---|---|---|---|---|---|---|---|---|
| | 1 | 2 | 3 | 6 | 8 | 10 | 14 | 17 |
| 1,000 ppm | 0 | 2 | 2 | 8 | 20 | 26 | 46 | 55 |
| 2,000 ppm | 1 | 2 | 3 | 22 | 36 | 52 | 65 | 69 |
| 4,000 ppm | 1 | 2 | 2 | 28 | 60 | 68 | 90 | 95 |

EXAMPLE 6

Topical Toxicity and Lethal Time Studies

Coptotermes formosanus Shiraki

Thirty worker Formosan subterranean termites were anaesthetized with gaseous carbon dioxide for 20 seconds before inoculation with a 0.5 ul droplet of an acetone solution of p-tolyl-diiodomethylsulfone at concentrations of zero to 4,000 ppm (in 400 ppm increments) and 6,000 to 10,000 ppm (in 2,000 ppm increments). A microapplicator (Model M, Instrumentations Specialities Co., Inc.) was used to administer the solution onto the insects' abdomens. The resultant doses were 0, 0.2, 0.4, 0.6, 0.8, 1.0, 1.2, 1.6, 1.8, 2.0, 3.0, 4.0 and 5.0 ug/termite. Treatments were replicated three times. The dose (ug/termite) was converted to ug/g using the mean worker biomass of this colony: $5.33 +/- 1.5$ 1 mg. Treated termites were transferred to a petri dish (5.0 cm diameter $\times$ 1.5 cm height) provisioned with two filter discs (Whatman No. 1) moistened with deionized water. Three soldiers were added to each unit to approximate colony soldier proportions. The experiment units were stored in an environmental chamber at $29° +/- 1°$ C. Dead or moribund workers were recorded and removed from each unit daily for 14 days. Mortality at 14 days was used to compute the topical $LD_{50}$ by probit analysis. The effective lethal time ($ELT_{90}$), defined as the time required by a fixed dosage of a toxicant to cause 90% mortality of termites was used to quantify lethal time.

The topical $LD_{50}$ of p-tolyl-diiodomethylsulfone against *Coptotermes formosanus* was estimated at 141.7 ug/g with 95% fiducial limits of 110.4–168.3 ug/g. The regression equation was $Y © 4.164 + 0.0060 \times (+/- 0.0007$ slope SE).

When administered topically, effects of p-tolyl-diiodomethylsulfone were fully expressed 14 days after the inoculation. At that time, only groups receiving more than 1.8 ug/termite (approximately 337.7 ug/g) exhibited mortality greater than or equal to 90%. The $ELT_{90}$s ranged from 8.4 to 18.9 days as shown in FIG. 1 below, indicating delayed activity of p-tolyl-diiodomethylsulfone against the Formosan termite.

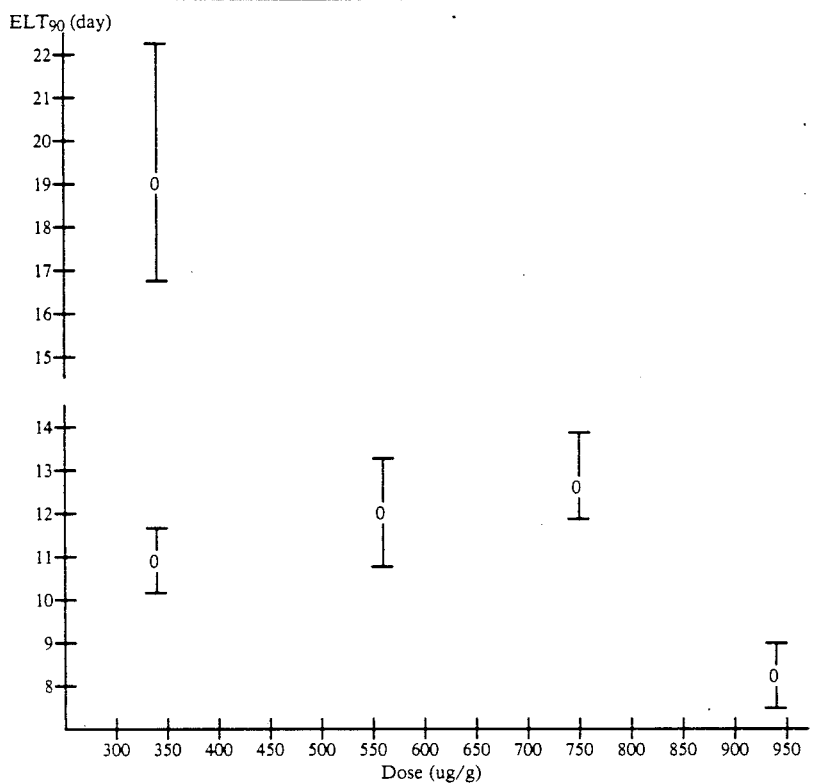

FIG. 1.
ELT₉₀ (X) ± 95% FL (U and L) for topical toxicity.

EXAMPLE 7

Slow-acting Antifeedant Bait Toxicant Testing

Reticulitermes virginicus

Laboratory tests with bait toxicants are designed to identify slow-acting chemicals and concentrations that have minimal antifeedant properties.

Chemicals exhibiting no activity on soil were tested using dyed alpha-cellulose as the substrate. Calco Oil Blue Dye (0.25 weight-percent) was used to color the cellulose so that feeding in treatments could be compared qualitatively with that in the controls. Test setups consisted of 30-ml containers (cups) having a small opening in the bottom. These were filled with a 1-cm layer of a labstone/gypsum mixture, which acted to "wick" water from a layer of moist cotton positioned under the cups. Approximately 0.1 g of treated cellulose was placed in each cup, and 25 worker termites (*Reticulitermes virginicus*) were added. All cups were kept within a larger container having a lid. Three replicates were established for the controls and for each of the treatment concentrations, which typically ranged from 12.5 to 5,000 ppm. Test units were examined over a 2-week period, with daily observations of the termites' behavioral and physical responses. Dead termites were removed at each examination to minimize fungal and bacterial contamination.

After two weeks' exposure to 5,000 ppm of the compound of Example 1, all termites were dead. In addition, termite survival was significantly reduced in treatments of the termites with ranges of 100 to 1,500 ppm of the compound of Example 1.

EXAMPLE 8

Gut Protozoa Studies on Termites

Reticulitermes virginicus

A series of foraging tests with p-tolyl-diiodomethylsulfone at low concentrations (25, 50, 75 and 100 ppm) were conducted in two nest chambers connected with tubing. One chamber contained an untreated wood block and 1000 *Reticulitermes virginicus* termites collected from a field colony. The second chamber contained a wood block, pre-decayed with the fungus *Gloeophyllum trabeum* and impregnated under vacuum with a solution of p-tolyl-diiodomethylsulfone in acetone, as described in ASTM standard D1413-61. The test was run for two weeks, after which time the termites hindguts were removed and the gut protozoas examined.

When compared to the controls, the numbers of protozoa in the termite hindgut were reduced by approximately 80 percent after exposure to 100 ppm of p-tolyl-diiodomethylsulfone for two weeks. Survival of these termites was slightly less than that of the controls at two weeks. However, with additional time, survival would be expected to be significantly reduced since termites cannot survive without their symbiotic protozoa, which digest cellulose. One specie of gut protozoan, *Personympha sp.*, was completely destroyed after two weeks. Because the termite requires all four species of protozoa present in the hindgut to survive, this destruction hastens mortality.

EXAMPLE 9

Testing Against German Cockroaches

Blattella germanica (Linnaeus)

Tests were conducted in circular glass containers which were kept in a dark room. The compound of Example 1 was blended with a 20% protein diet at a level of 40,000 ppm. Fifty Blattella germanica cockroaches were fed this diet, and another 50 control cockroaches were fed the untreated protein diet. Mortality counts were taken on the 6th, 13th, 20th, 27th, and 34th day. Total weight of all surviving cockroaches was divided by the number of cockroaches in each group to give an average weight for both the treated group and the control group. The results are shown in Table 3 below. On average, the weight of the control cockroaches increased sevenfold while the weight of the cockroaches fed p-tolyl-diiodomethylsulfone did not quite double, and nearly total mortality resulted, in the same time period.

TABLE 3

| | 20% Protein Diet with 40,000 ppm p-Tolyl-diiodomethylsulfone | | 20% Protein Diet (Control) | |
|---|---|---|---|---|
| Number of Days | Surviving Cockroaches | Average Weight (mg) | Surviving Cockroaches | Average Weight (mg) |
| 0 | 50 | 9.2 | 50 | 9.6 |
| 6 | 47 | 9.6 | 46 | 13.3 |
| 13 | 38 | 10.8 | 39 | 22.3 |
| 20 | 27 | 11.9 | 32 | 39.7 |
| 27 | 9 | 15.6 | 31 | 46.5 |
| 34 | 2 | 15.0 | 23 | 66.5 |

Two replications were run subsequently, utilizing in each instance 50 Blattella germanica second-instar nymphs for both the treatment group and the control group. The results are summarized in Tables 4 and 5 below.

TABLE 4

| | 20% Protein Diet with 40,000 ppm p-Tolyl-diiodomethylsulfone | | 20% Protein Diet (Control) | |
|---|---|---|---|---|
| Number of Days | Surviving Cockroaches | Average Weight (mg) | Surviving Cockroaches | Average Weight (mg) |
| 0 | 50 | 3.2 | 50 | 3.2 |
| 10 | 46 | 3.5 | 44 | 10.2 |
| 17 | 16 | 4.4 | 36 | 14.4 |
| 24 | 5 | 4.0 | 27 | 23.0 |
| 31 | 5 | 4.0 | 22 | 40.0 |
| 38 | 1 | 10.0 | 22 | 43.6 |
| 45 | 1 | 10.0 | 19 | 60.6 |
| 52 | 0 | — | 18 | 62.8 |

TABLE 5

| | 20% Protein Diet with 40,000 ppm p-Tolyl-diiodomethylsulfone | | 20% Protein Diet (Control) | |
|---|---|---|---|---|
| Number of Days | Surviving Cockroaches | Average Weight (mg) | Surviving Cockroaches | Average Weight (mg) |
| 0 | 50 | 3.6 | 50 | 4.0 |
| 10 | 45 | 4.0 | 45 | 10.2 |
| 17 | 23 | 4.4 | 39 | 15.6 |
| 24 | 10 | 5.0 | 30 | 22.0 |
| 31 | 6 | 5.0 | 27 | 37.4 |
| 38 | 2 | 10.0 | 23 | 43.0 |
| 45 | 0 | — | 21 | 55.2 |
| 52 | | | 20 | 57.0 |

TABLE 5-continued

For the control group, molting occurred at 5 weeks, and males and females could be identified and counted. Nymphs treated with p-tolyl-diiodomethylsulfone never reached the adult state.

EXAMPLE 10

Behavioral and Repellency Cockroach Tests

Blatella germanica

One hundred European cockroaches (40 adults, 60 nymphs) were introduced into a squared arena (52.5 cm × 42.5 cm) maintained in total darkness. The inner sides were covered with liquid Teflon$^R$ nonstick coating to prevent escape. Two baits, one control bait and one containing 40,000 ppm p-tolyl-diiodomethylsulfone, were introduced into the arena. Photographs using a flashlight were made every ten minutes during a period of 12 hours. The distribution of individual cockroaches was noted and statistically analyzed.

It was determined that the cockroaches followed their normal activity rhythm in the arena. The general dispersion of cockroaches increased from the center of the arena to the edges (aggregation) and two linear regression curves showing the dispersion around treated and untreated baits were similar. There was no statistical difference between the mean number of cockroaches at 5 and 10 cm from the control bait and the treated bait, respectively, nor was there any statistical difference between the mean number of cockroaches feeding on the two baits.

Thus, at a level of 40,000 ppm, p-tolyl-diiodomethylsulfone neither repels nor attracts Blatella germanica.

The foregoing is merely illustrative of the invention and is not intended to limit the invention to the disclosed compounds. Variations and changes which are obvious to one skilled in the art are intended to be within the scope and nature of the invention as defined in the appended claims.

What is claimed is:

1. A method of killing insects from the group consisting of termites, cockroaches and ants, comprising treating said insects with an insecticidal amount of a composition consisting essentially of from about 25 ppm to about 80,000 ppm of a diiodomethylsulfone compound of the formula:

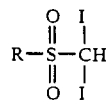

wherein R is $R_1$ $(CH_2)_n$, wherein n is 0 to 4 and $R_1$ is loweralkyl, phenyl, monoloweralkylphenyl, monoalophenyl, nitrophenyl, aminophenyl, acetamido-substituted phenyl, $(CH_2)_m$COOH substituted phenyl wherein m is 1 to 3, disubstitutedhalophenyl, (halo)(nitro)phenyl, (nitro)(loweralkyl)phenyl, (halo)(loweralkyl)phenyl or disubstituted-loweralkylphenyl and a diluent.

2. The method of claim 1 wherein n is 0 and $R_1$ is p-tolyl.

3. The method of claim 1 or claim 2 wherein said termites are Formosan subterranean termites and the composition contains from about 200 ppm to about 4,000 ppm of said compound.

4. The method of claim 1 or claim 2 wherein said termites belong to the genus Reticulitermes and the composition contains from about 25 ppm to about 800 ppm of said compound.

5. A method of killing cockroaches comprising treating said cockroaches consisting essentially of from about 10,000 ppm to about 80,000 ppm of a compound of the formula:

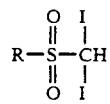

wherein R is $R_1(CH_2)n$, wherein n is 0 to 4 and $R_1$ is loweralkyl, phenyl, monoloweralkylphenyl, monohalophenyl, nitrophenyl, aminophenyl, acetamido-substituted phenyl, $(CH_2)_m COOH$-substituted phenyl wherein m is 1 to 3, disubstitutedhalophenyl, (halo)(nitro)phenyl, (nitro)(loweralkyl)phenyl, (halo)(loweralkyl)phenyl or disubstitutedloweralkylphenyl, and a diluent.

6. The method of claim 5 wherein n is 0 and $R_1$ is p-tolyl.

7. A method of killing ants comprising treating said ants with a composition consisting essentially of from about 10,000 ppm to about 40,000 ppm of a compound of the formula:

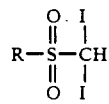

wherein R is $R_1(CH_2)n$, wherein n is 0 to 4 and $R_1$ is loweralkyl, phenyl, monoloweralkylphenyl, monohalophenyl, nitrophenyl, aminophenyl, acetamido-substituted phenyl, $(CH_2)_m COOH$-substituted phenyl wherein m is 1 to 3, disubstitutedhalophenyl, (halo)(nitro)phenyl, (nitro)(loweralkyl)phenyl, (halo)(loweralkyl)phenyl or disubstitutedloweralkylphenyl, and a diluent.

8. The method of claim 7 wherein n is 0 and $R_1$ is p-tolyl.

9. The method of claim 7 or claim 8 wherein said ants are carpenter ants.

10. The method of claim 7 or claim 8 wherein said ants are fire ants.

* * * * *